United States Patent
Stormbom

(10) Patent No.: US 6,564,633 B2
(45) Date of Patent: May 20, 2003

(54) MEASUREMENT METHOD AND SYSTEM FOR A HUMIDITY OR GAS CONCENTRATION SENSOR

(75) Inventor: Lars Stormbom, Helsinki (FI)

(73) Assignee: Vaisala Oyj, Helsinki (FI)

( * ) Notice: Subject to any disclaimer, the term of this patent is extended or adjusted under 35 U.S.C. 154(b) by 64 days.

(21) Appl. No.: 09/731,735

(22) Filed: Dec. 8, 2000

(65) Prior Publication Data

US 2001/0003249 A1 Jun. 14, 2001

(30) Foreign Application Priority Data

Dec. 9, 1999 (FI) .............................. 19992651

(51) Int. Cl.$^7$ .............................................. G01N 19/10
(52) U.S. Cl. ................. 73/335.05; 73/335.04; 73/29.02; 73/1.06
(58) Field of Search ....................... 73/1.06, 29, 335.02, 73/335.03, 335.05, 335.04

(56) References Cited

U.S. PATENT DOCUMENTS

| | | | | |
|---|---|---|---|---|
| 3,825,756 A | * | 7/1974 | Weiss | 250/343 |
| 4,759,210 A | * | 7/1988 | Wohltjen | 73/31.07 |
| 5,033,284 A | | 7/1991 | Belt et al. | 73/1.06 |
| 5,307,668 A | * | 5/1994 | Vander Heyden | 73/30.02 |
| 5,792,938 A | | 8/1998 | Gokhfeld | 73/29.02 |
| 5,816,705 A | * | 10/1998 | Vander Heyden et al. | 374/37 |

* cited by examiner

Primary Examiner—Helen Kwok
Assistant Examiner—David Rogers
(74) Attorney, Agent, or Firm—Birch, Stewart, Kolasch & Birch, LLP

(57) ABSTRACT

A method and system relating to an improvement in measuring accuracy of a gas concentration sensor, the method comprising the steps of measuring a parameter of the sensor, the parameter being a resistance or a capacitance, that is sensitive to the gas or its concentration being measured, and simultaneously changing the temperature of the sensor in a cyclic manner. The parameter of the sensor being measured is measured more than two times or continuously during each heating cycle. The measured parameter value is filtered to obtain a signal component associated with the fundamental frequency of the heating cycle for use at a later step, and the thus filtered signal component is used in the correction and/or calibration of actual output signal of the sensor.

20 Claims, 2 Drawing Sheets

MEASUREMENT METHOD AND SYSTEM FOR A HUMIDITY OR GAS CONCENTRATION SENSOR

BACKGROUND OF THE INVENTION

1. Field of the Invention

The present invention relates to a measurement method and system for use in conjunction with a humidity or gas concentration sensor.

2. Description of Background Art

U.S. Pat. No. 5,033,284 discloses a calibration method, wherein a correction factor of the sensor reading can be computed by way of transiently deviating the temperature of the humidity or gas concentration sensor. This method is applicable to an automatic self-test of the measurement device at intermittent intervals. In the method, the partial pressure of the gas under measurement is assumed to stay constant during imposed deviation of the sensor temperature.

During normal function of the device, the reading can be updated quite frequently within the confines set by the measurement noise. However, as the self-calibration step takes a relatively long time and excludes simultaneous measurement operation of the device, the self-calibration step can be carried out only infrequently. Hence, if the partial pressure of the gas under measurement does not remain constant during the self-calibration step, an erroneous correction is made on the device reading until the next self-calibration is performed. During the self-calibration step, the measurement noise can be filtered extremely effectively, for example, by way of taking a plurality of measurement values during the temperature change, and then applying the least squares method to fit a linear or polynomial response function with the measurement data.

U.S. Pat. No. 5,792,938 (Gokhfeld) relates to a moisture measurement method using a humidity sensor, wherein the sensor response is measured at two different temperatures, and the measurement value difference or slope of response function is directly used as the output signal of the device.

This method is not problematic with regard to changes in water vapor partial pressure during the measurement cycle. However, in this case, the measurement noise causes a larger error in the output signal as compared with other techniques if the measurements are taken at only two points. Furthermore, the method involves a long update period of output signals even in normal operation, not merely during the self-calibration step, as is the case in U.S. Pat. No. 5,033,284, described above.

Both of the above-describe methods are capable of reducing offset errors that occur in measurement devices due to calibration error or instability.

SUMMARY AND OBJECTS OF THE INVENTION

It is an object of the present invention to provide an entirely novel method capable of overcoming the drawbacks of the above-described prior art techniques.

This and other objects are achieved using a method wherein the temperature of the humidity or gas concentration sensor is changed cyclically, and the response to the temperature change is measured in the sensor output signal. Herein, the temperature cycle has a certain specific fundamental frequency $\omega_s$. During temperature cycling, sensor response to temperature change is measured (typically from its capacitance or resistance); that is, sensor response (as its capacitance or resistance change) is measured repeatedly as a function of the temperature change. Next, a sensor output signal or a variable (such as relative humidity) computed from the output. signal is subjected to a frequency spectrum analysis, and frequency components different from the fundamental frequency of the temperature cycling sequence are filtered away. A typical humidity sensor has an almost constant capacitance irrespective of the temperature if the relative humidity (RH) is constant. With constant partial pressure of the water vapor, however, the RH varies during the temperature cycling as:

$$RH = P_w / P_{ws}(T) \cdot 100\%,$$

where $P_w$ = water vapor pressure and $P_{ws}(T)$ = water vapor saturation pressure.

The basic concept of the present invention is to keep the fundamental frequency of the temperature cycling sequence so low that the humidity sensor can stabilize during changes. In other words, the sensor frequency response is adapted to extend beyond the fundamental frequency of the temperature cycling sequence.

If temperature cycling is performed at a frequency whose fundamental component substantially exceeds the frequency response of the sensor (which may be difficult to arrange with concurrent sensors), temperature cycling only affects the sensor's temperature dependence.

The frequency dependence of the sensor response can be detected from the phase shift with regard to the sensor heating signal. If the sensor has a fast response, there is no additional phase shift. If the sensor has a slow response or if the cycling sequence has a higher fundamental frequency, the phase lag in the sensor output signal becomes larger. When the fundamental frequency of the temperature cycling sequence is equal to the cutoff frequency of the sensor's frequency response, the phase lag becomes equal to 45°. Simultaneously, the sensor output signal level begins to fall. In principle, the phase lag can be utilized to compute the response of an ideally fast sensor. Hence, it may be contemplated that this effect could indicate the point at which the sensor due to, e.g., soiling has become so slow as to need servicing.

The result of the frequency spectrum analysis is a basic measurement device response signal from which the sensor output signal is processed and which indicates the measured gas concentration or humidity.

The frequency analysis can be performed electronically utilizing analog techniques, e.g., employing bandpass filters, or digitally through a Fourier transform analysis, e.g., by way of an FFT algorithm.

The method may also be used for self-calibration, whereby the result of the cycling sequence is utilized to compute a corrected measurement device output signal.

The method and system according to the invention offer significant benefits.

Using the method of the present invention, it is possible to take continuous measurements without separate calibration steps, achieving more accurate and stable measurement results than those obtained by prior art methods. Furthermore, the invention can be employed to obtain additional sensor readings in order to improve long-term stability. The temperature sensitivity of the sensor may be monitored in realtime, and corrections can be made if temperature sensitivity changes from its default value.

BRIEF DESCRIPTION OF THE DRAWINGS

The present invention will become more fully understood from the detailed description given hereinbelow and the accompanying drawings, which are given by way of illustration only, and thus are not limitative of the present invention, and wherein.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Figure 1:
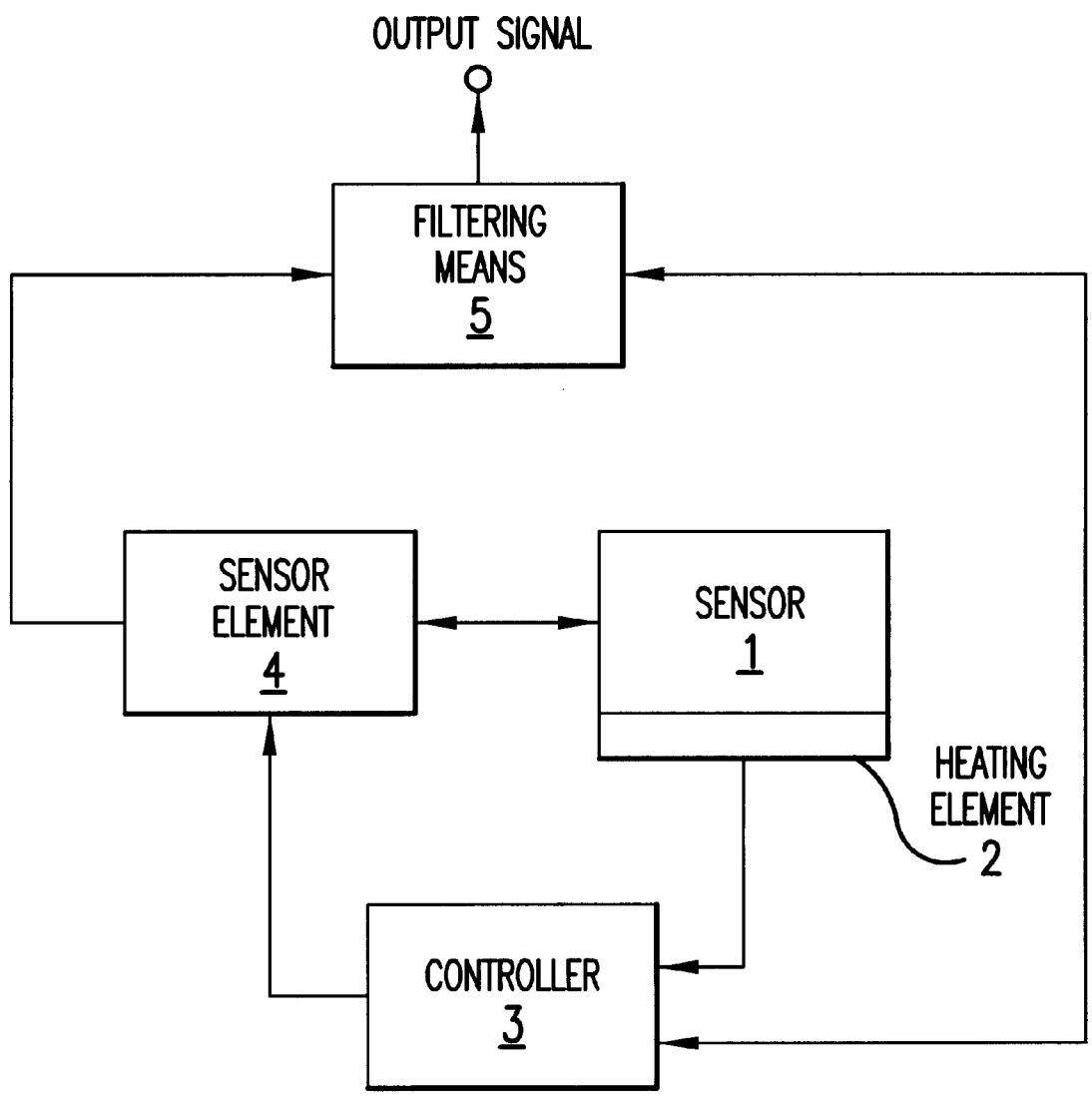
FIG. 1 is a block diagram of a system according to the invention.

Referring to FIG. 1, the system according to the invention shown therein comprises a gas concentration sensor 1 for measuring the relative humidity of ambient air. The sensor 1 may be, e.g., a capacitive sensor or a resistive gas concentration sensor. A heating and/or cooling element 2 is connected to the sensor 1, and the heating or cooling effect is controlled by a controller 3. The element 2 may be either a conventional resistor or a Peltier element that also is capable of cooling the sensor. A sensor parameter (such as capacitance or resistance) sensitive to the variable being measured by the sensor is detected by a sensor element 4, and the measurement is advantageously synchronized to the control sequence of the heating cycle controller 3. From the measured value of the sensor parameter (capacitance or resistance), an actual measurement signal is generated that is proportional, generally in a linear or at least quasilinear manner, to the absolute or relative concentration of the gas being measured. A typical gas concentration measurement is the measurement of relative humidity, wherein the gas component being measured is water vapor. The variable being measured is subjected to a frequency spectrum analysis in unit 5, using either by software means (Fourier transform analysis), or by using electronic filters. According to the invention, the controller 3 is adapted to control the heating element by heating pulses repeating at preset intervals and having a controllable waveform in terms of, e.g., pulse width, height, or shape. The invention also covers the option of varying the interval between successive heating pulses, that is, the repetition rate of the heating control waveform. According to a preferred embodiment of the invention, the temperature of the sensor 1 is made to vary in a sinusoidal manner that can be implemented using a half-wave rectified sinusoidal heating power signal. The maximum frequency of the heating power input is chiefly determined by the thermal properties of the sensor 1. The larger the thermally radiating and/or conductive surface area of the sensor 1 per its mass unit, the higher the heating frequency. Obviously, the heating element 2 must have a sufficiently high dissipation capability in order to elevate the sensor temperature during each half-cycle. Also, the time constant of the sensor's gas concentration detection response must be sufficiently short relative to the duration of the heating cycle in order to avoid problems associated with extra delays. In practice, the time constant of the sensor response should not exceed ¼ to ⅓ of the half-cycle duration of the heating period; otherwise, special action, based on such data as the phase-shift information, must be taken to obtain a reliable measurement result.

The most advantageous embodiment of the invention is carried out by simultaneously measuring both the response of the sensor 1 to a varying temperature and the internal temperature of the sensor 1 during the thermal heating cycle. This allows the system to perform identical frequency spectrum analyses on both the sensor response and the sensor internal temperature. The temperature signal frequency component at the fundamental frequency of the heating cycle is denoted by $t(\omega_s)$, and the sensor response signal frequency component at the fundamental frequency of the heating cycle is denoted by $s(\omega_s)$. Then, a ratio $s(\omega_s)/t(\omega_s)$ may be computed by means of the controller 3 and spectrum analysis unit 5 that stays at least essentially constant if the temperature change during the heating cycle for any reason (such as sensor soiling or change of heating power) deviates from its normal value.

Generally, the average value of the sensor temperature over the heating cycle is also needed to generate the corrected sensor output signal.

The frequency analysis may be carried out after each measurement sequence, whereby the measurement device output signal can be updated at a faster rate than that of the sensor temperature control cycle.

In its simplest form, the frequency spectrum analysis may be performed as a phase-locked measurement implemented with the help of units 3 and 5, whereby the result of the frequency spectrum analysis is a signal indicating the temperature sensitivity of the sensor response to the variable being measured.

Figure 2:
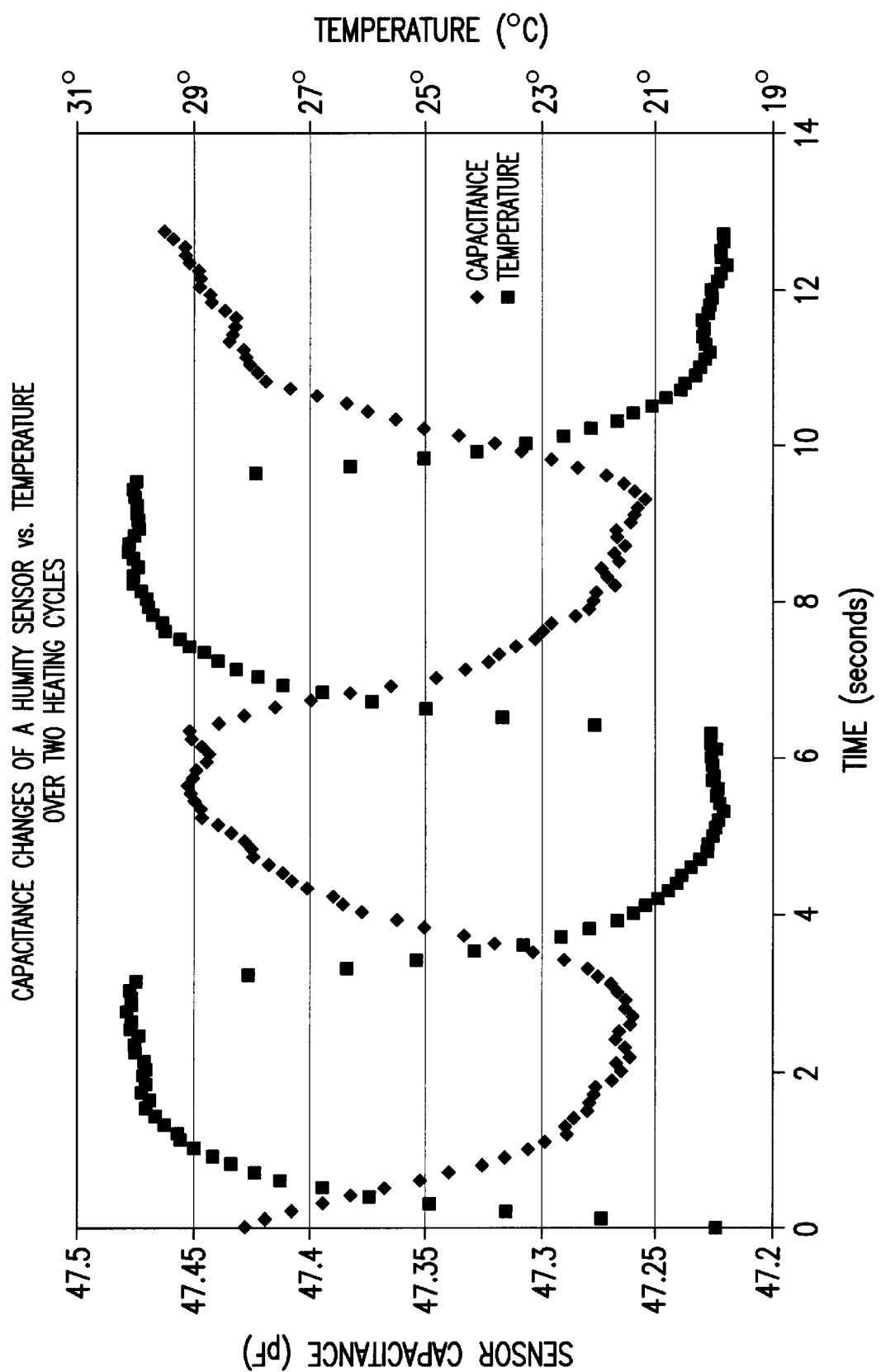
FIG. 2 is a graph wherein is plotted one measurement session according to the invention.

In FIG. 2 a graph plots temperature and capacitance changes of a capacitive humidity sensor over approximately two measurement cycles. As can be seen from the graph, there is an about 180° phase shift between the capacitance of the capacitive humidity sensor and the temperature of the capacitive humidity sensor. Without departing from the scope and spirit of the invention, it may be contemplated to use this phase-shift information to detect, e.g., sensor delay or need for servicing. In the context of the invention, the term "heating rate" refers to the inverse value of the time interval between two successive maxima of the sensor temperature curve that, in the case illustrated in the-graph, gives a heating rate of about 0.15 Hz.

Particularly advantageously, the invention can be applied to transducers having an essentially linear or possibly even negligible response to temperature variations in their normal operating state. Transducers of this kind are, e.g., capacitive humidity sensors based on a polymer dielectric insulator, such as those commercially available under trade mark Humicap®.

According to a preferred embodiment of the invention, the heating controller is used to provoke at least one specific calibration cycle during which the heating/cooling effect is driven higher than the level used during a normal measurement cycle. This arrangement allows a humidity sensor system to reach either an entirely dry humidity point of 0% RH or a dew point (100% RH), or possibly even both of these points.

According to another preferred embodiment of the invention, the strongest signal component is detected from the frequency spectrum analysis of the temperature dependence response, and said signal component is used in the measurement of the variable derived from the frequency analysis of the sensor response or, alternatively, in the computation of the correction term required for display of the measurement device reading.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for measuring a variable of gas concentration, comprising the steps of:
   changing a temperature of a sensor (1) that is sensitive to a gas or its concentration in a cyclic manner, each change in said cyclic manner being a heating cycle;
   measuring a parameter of the sensor more than two times during each heating cycle;
   converting the measured value of the parameter into an actual output signal of the variable of the gas concentration being measured, the output signal then being proportional to the measured variable of the gas concentration;
   filtering the measured parameter value to obtain a signal component associated with a fundamental frequency of the heating cycle, the filtered signal component being used as an actual output signal of the sensor or for calibrating said output signal of said sensor without a separate calibration step; and
   performing a frequency analysis after each measurement sequence, and where the actual output signal is updated at a frequency faster than the frequency of the heating cycle.

2. The method according to claim 1, further including measuring the temperature of the sensor (1), and performing a filtration operation on a frequency associated with the repetition rate of the heating cycle.

3. The method according to claim 2, wherein the converting step includes computing a ratio of the sensor temperature value to the measured parameter value or values of the sensor (1) obtained by said filtering means.

4. The method according to claim 3, wherein an average temperature of the sensor during the heating cycle is used when measuring the variation of the gas concentration or in calibrating the measurement device.

5. The method of claim 1, wherein the filtering is performed using an analog technique with a bandpass filter.

6. The method according to claim 1, wherein the filtering is performed using a digital technique, the digital technique being a Fourier transform analysis.

7. The method according to claim 1, wherein the sensor is a capacitive humidity sensor.

8. The method according to claim 1, wherein the parameter of the sensor (1) is a resistance or a capacitance.

9. The method according to claim 1, wherein the variable of the gas concentration being measured is relative humidity.

10. The method according to claim 1, wherein the parameter of the sensor (1) is measured continuously.

11. The method according to claim 1, wherein a period of the heating cycle is from 4 to 8 times a time constant of the sensor.

12. the method according to claim 1, wherein said filtering step is performed at least 16 times per said heating cycle, thereby updating said actual output signal faster than said heating cycle.

13. A system for measuring a gas concentration, comprising:
   a gas concentration sensor (1), said sensor (1) being a resistance or capacitance sensor for measuring gas or its concentration and generating a parameter proportional to the gas concentration being measured;
   heating/cooling means (2) thermally connected to the gas concentration sensor (1);
   means (3) for controlling said heating/cooling means for providing cyclical heating of the sensor (1);
   a measurement apparatus (4) for measuring the value of the parameter of the resistance or capacitance sensor more than two times during each heating cycle; and
   filtering means for isolating signals at a fundamental frequency during said cyclic heating of the sensor to obtain an output signal or a signal for calibrating said system without a separate calibration step, and for performing a frequency analysis after each measurement sequence, and where the frequency to update the actual output signal from the filtering means is faster than the frequency of the heating cycle.

14. The system according to claim 13, further comprising means for simultaneously measuring the temperature of the sensor (1) and measuring the parameter value of the sensor, and means for filtering the temperature measurement values at the fundamental frequency of the heating cycle repetition rate.

15. The system according to claim 13, wherein said filtration means are implemented using an analog technique with a bandpass filter.

16. The system according to claim 13, wherein said filtration means are implemented using a digital technique, the digital technique being a Fourier transform analysis.

17. The system according to claim 13, further comprising means for computing a ratio of a sensor temperature value to the measurement signal value or values of the sensor (1) obtained by said filtering means.

18. A system according to claim 17, further comprising means for utilizing an average value of the sensor temperature during the heating cycle of the measurement device.

19. The system according to claim 13, wherein a period of the heating cycle is from 4 to 8 times a time constant of the sensor.

20. The system according to claim 13, wherein said filtering means is capable of updating said actual output signal at least 16 times per said heating cycle.

* * * * *